(12) United States Patent
Lauritsen et al.

(10) Patent No.: US 6,456,197 B1
(45) Date of Patent: Sep. 24, 2002

(54) OIL-IN-WATER DETECTOR BUOY ARRANGEMENT

(75) Inventors: Glen R. Lauritsen, Houston, TX (US); Brent A. Salyer, Houston, TX (US)

(73) Assignee: FMC Technologies, Inc., Chicago, IL (US)

( * ) Notice: Subject to any disclaimer, the term of this patent is extended or adjusted under 35 U.S.C. 154(b) by 0 days.

(21) Appl. No.: 09/275,609

(22) Filed: Mar. 24, 1999

Related U.S. Application Data

(60) Provisional application No. 60/079,284, filed on Mar. 25, 1998.

(51) Int. Cl.⁷ .................................................. G08B 1/08
(52) U.S. Cl. ......................... 340/539; 340/603; 73/451
(58) Field of Search ................................ 340/511, 537, 340/603, 627, 631, 539; 73/32 R, 451

(56) References Cited

U.S. PATENT DOCUMENTS

| 5,444,383 A | 8/1995 | Agar et al. |
| 5,532,679 A | * 7/1996 | Baxter .......................... 340/539 |

OTHER PUBLICATIONS

Agar Technologies, Ltd., Agar Leakwise® ID–227 Oil Sheen Monitoring System For Marine Applications, Brochure, Agar Corporation, Houston, Texas, U.S.A.

* cited by examiner

*Primary Examiner*—Daryl Pope
(74) *Attorney, Agent, or Firm*—Gary L. Bush; Andrews & Kurth, Mayor, Day & Caldwell, LLP

(57) ABSTRACT

A self-righting buoy having an oil/water sensor is provided which includes a radio transmitter or signaling beacon to trail a loading hose or a potential source of leaking oil, such as a FPSO, down current for remote detection of oil sheens.

13 Claims, 3 Drawing Sheets

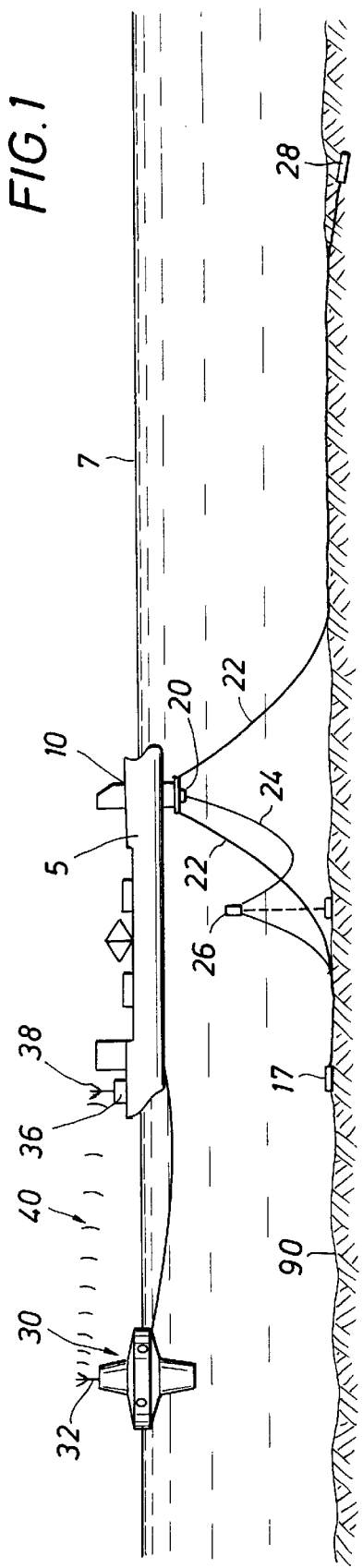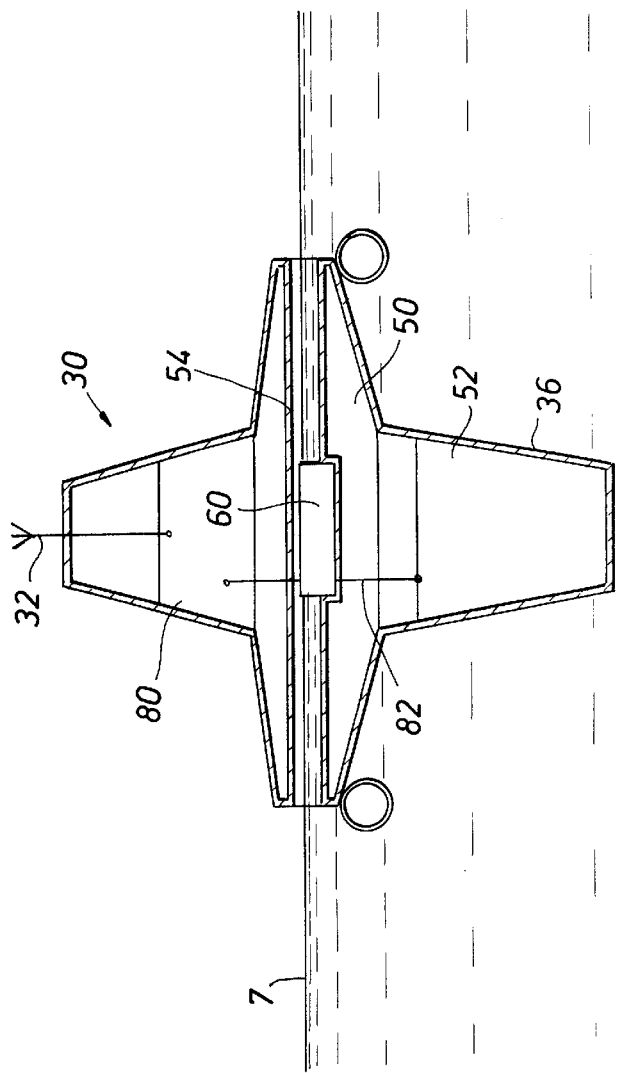

OIL-IN-WATER DETECTOR BUOY ARRANGEMENT

REFERENCE TO PROVISIONAL APPLICATION

The priority of U.S. Provisional Application No. 60/079,284 filed on Mar. 25, 1998 is claimed.

BACKGROUND OF THE INVENTION

1. Field of the Invention

This invention relates generally to the field of offshore transfer of hydrocarbons from a subsea well to a Floating Oil Storage or Production (FPSO) Vessel or between a pipeline and a CALM buoy and swivel and a tanker. In particular, the invention concerns detection of floating oil on the sea surface where the oil leaks from the connection of an oil conduit connected between an oil storage vessel for subsea wells or between a tanker and a subsea pipeline.

2. Description of the Prior Art

Environmental concerns make it increasingly important that any oil that might be leaking from a connection of an oil transfer riser to a storage or production vessel or between a tanker and a subsea pipeline be quickly detected in order that corrective action may be taken immediately.

Oil-in-water detection apparatus exists for determining the presence of hydrocarbons floating on water. For example AGAR Technologies, Ltd. of Houston, Tex., commercially offers an oil-in-water sensor based on the principle of electromagnetic absorption. Such sensor comprises a very high frequency transmitter connected to a mismatched antenna. The antenna is immersed in water with oil floating on it. The higher the energy absorption of the fluid, the more the loading of the antenna, and therefore, the more energy which must be applied to the transmitter. Water absorbs much more energy than does oil (or other insulating materials such as air, glass, plastic, etc.). If the antenna is surrounded by an oil/water mixture, the loading is proportional to the water content. Thus, an instrument based upon antenna loading is capable of detecting very small thickness oil sheens floating on water. It is also capable of monitoring the thickness of a layer of oil on water.

The AGAR Company mentioned above commercially provides a flotation device or buoy on which a sensor as described above is mounted. Such flotation device is designed for offshore waters near oil tanker terminals to detect floating oil sheens resulting from spills or leaks which may occur during the loading/unloading process of tankers. Nevertheless, several deficiencies have been identified with AGAR arrangement when used in certain mooring applications.

The AGAR buoy is connected to a vessel by a tether which includes an electrical cable, typically 10 min length. Such cable provides electrical power to the oil/water sensor mounted on the buoy and provides a signal path between the sensor and the tanker. But, an electrical cable running between the vessel and the AGAR buoy has safety deficiencies where oil spills are involved. Furthermore, the AGAR buoy on which its sensor is mounted is not self-righting which is a disadvantage where extremely rough seas are encountered.

In view of the disadvantages identified above, the AGAR buoy and sensor is not ideally suitable for the detection of oil leaking into the sea for a tanker vessel moored to a CALM buoy or to a single point mooring loading system for a floating oil storage or production vessel, because it is dependent on an electrical cable for power and communication and its buoy configuration is not self-righting.

3. Identification of Objects of the Invention

A primary objective of this invention is to provide an improved oil-in-water detector buoy for detecting oil on the surface of the sea where offshore single point mooring terminals are being utilized. Due to the natural orientation behavior of a ship at a single point mooring, all oil leakage or spills will eventually be carried by the ocean current and/or winds which is orienting the ship, past a buoy tethered to the ship and held down-current by the same ocean currents. Leakage from the subsea risers and both subsea and floating hoses and the mechanical components of the terminals will be carried to the buoy by the ocean currents.

A further object of the invention is to provide an oil-in-water detector that is self powered, transmits its oil/water information via radio to a ship board antenna, and is mounted on a self-righting buoy capable of withstanding high seas.

SUMMARY OF THE INVENTION

An oil-in-water detector is mounted on a self-righting buoy which is battery powered and includes an electromagnetic antenna for transmitting radio signals representative of the oil/water ratio sensed by the detector. In one embodiment the heavy batteries are mounted in a bottom pod of the buoy thereby contributing to the self-righting characteristics of the buoy. In another embodiment, concrete or other heavy ballast material is provided in the bottom pod, and the batteries are placed at other locations of the buoy. The oil/water detector may be tethered behind a FPSO vessel or behind the "U" of floating hoses of a tanker moored and loaded via a CALM system. The oil/water detector buoy may be tethered to any offshore or water location requiring oil detection where the combined features of self-contained powering, self righting and radio transmitted signals are desired over existing units which do not offer these features. Such locations include use with a spread moored vessel, a marine loading arm terminal, a pier or jetty or an offshore floating or fixed structure for a hydrocarbon well. Alternatively, a beacon signal such as a strobe light or horn may be used in place of a radio transmitted signal on the oil/water detector buoy.

BRIEF DESCRIPTION OF THE DRAWINGS

The objects, advantages, and features of the invention will become more apparent by reference to the drawings which are appended hereto and wherein like numerals indicate like parts and wherein an illustrative embodiment of the invention is shown, of which:

FIG. 1 is a diagrammatic illustration of a buoy-mounted oil/water detector trailing a storage vessel which is moored at sea and is configured to load oil via a subsea riser system from a subsea well;

FIG. 2 is an enlarged illustration of the oil/water detection buoy;

DESCRIPTION OF THE INVENTION

Figure 3:
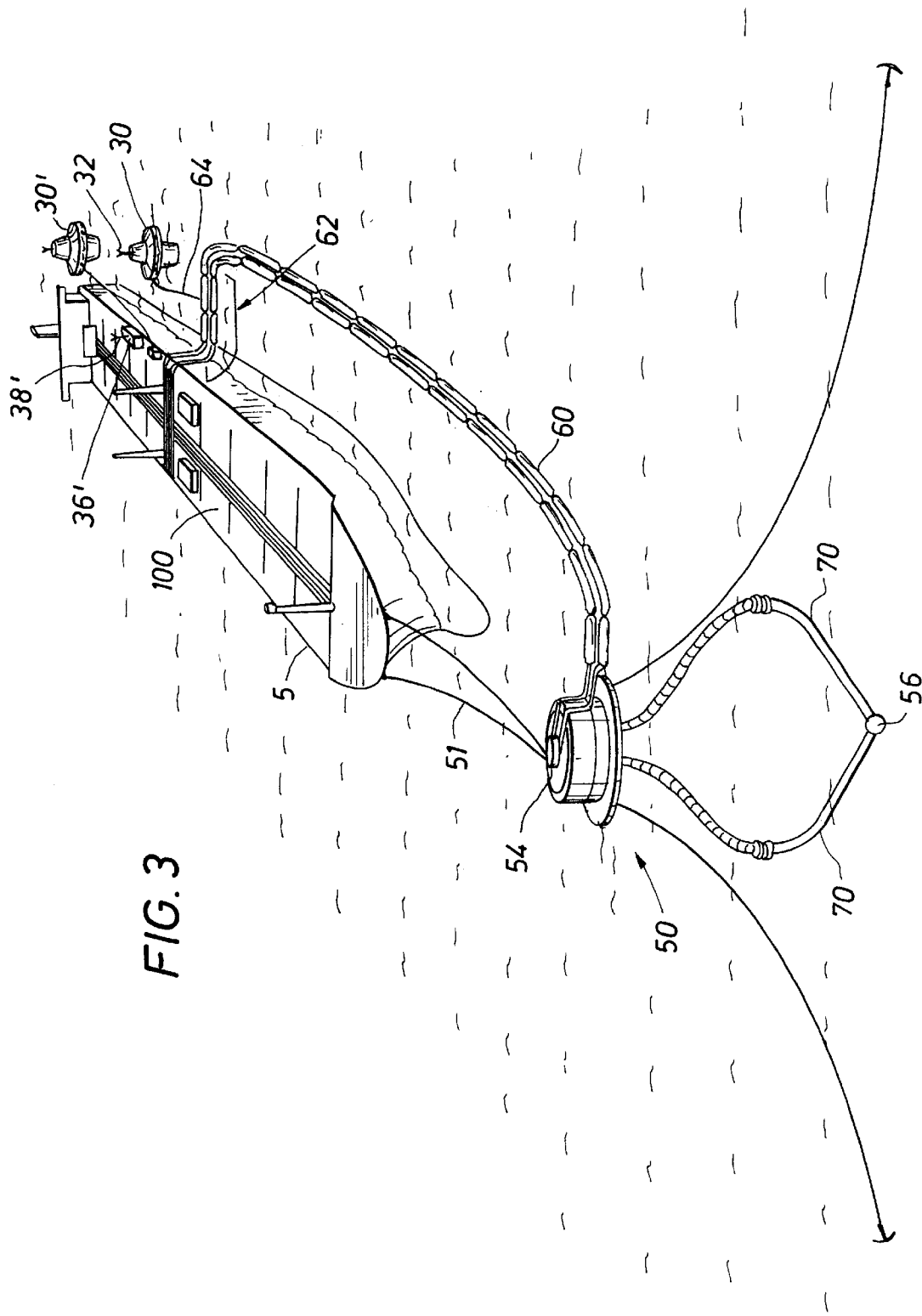
FIG. 3 is an illustration of the invention where an oil/water detection buoy is tethered down current of the "U" position where floating hoses enter a tanker moored by a CALM buoy at an offshore loading/unloading terminal.

FIGS. 1 and 2 illustrate an oil/water detector system 30 mounted on a buoyant buoy 50 which is connected to a Floating Production and Storage (FPSO) Vessel 5. Such vessel may be moored as in FIG. 1 where the vessel 5 floats on the sea surface 7 and is rotatably secured to a turret system 10 which is anchored by anchor legs 22 to anchors 28 on the sea bead 90. A riser 24 is connected between a subsea well 17 and the turret system 10. The mooring system of FIG. 1 may be of the disconnectable type or the storage vessel 5 may be permanently moored via a turret or other single point mooring device. Oil that spills from the connection of riser 24 to the vessel may be detected with oil/water detector buoy 30.

The oil/water detector buoy 30 of the invention is tethered by means of a line or tether 34 behind a vessel 5. If hydrocarbons leak from the riser 24 or turret 10, such hydrocarbons will flow past the stem of the vessel 5 due to the sea currents and/or wind into which the vessel is heading. The oil/water detector buoy will be in the path of such hydrocarbons, because as the vessel 5 weathervanes about turret 10, the oil/water detector trails the vessel and remains in the path of the floating hydrocarbons.

FIGS. 1 and 2 illustrate the salient features of the oil/water detector according to the invention. The buoy 30 is configured to be a self-righting buoy in order to survive heavy seas. Buoyancy of the buoy is provided with flotation material or by water-tight, air-filled spaces. The sensor 60 is electrically powered by on-board batteries 52, which as illustrated in FIG. 2, are mounted in a bottom pod 36 of the buoy 50. Alternatively, bottom pod 36 may be filled with a heavy material such as concrete for ballasting the buoy 50 with the batteries placed elsewhere on the buoy.

An oil/water sensor 60, is placed in a channel 54 through which sea water (possibly contaminated by leaking hydrocarbon crude oil) passes through. The channel 54 is designed in coordination with the buoyancy of the buoy 50 to be at the same height as the sea surface 7. The sensor 60 preferably includes a very high frequency transmitter connected to a mismatched antenna submerged in the sea water 7. The principle of operation of the sensor is the same as that of an AGAR LEAKWISE® ID-227 Oil Sheen Monitoring System sold by AGAR Technologies, Ltd. of Houston, Tex.

The sensor 60 is powered by batteries 52 which are mounted and self contained on the buoy 50 as explained above. Dashed line 82 schematically indicates the power communication path between batteries 52, sensor 60 and an electronics module 80 which is coupled to sensor 60 and to batteries 52 for measuring the oil/water ratio of sea water in channel 54. Electronic module 80 is arranged and designed to apply a signal representative of that ratio to an electromagnetic antenna 32, whereby radio waves 40 are broadcast for being received by antenna 38 and receiving electronics 36 on board vessel 5.

FIG. 3 illustrates a CALM buoy 50 to which a tanker 100 is tethered by mooring lines 51. Such lines 51 may be rigid or flexible. Loading hoses 70 run from a conduit 56 to swivel 54 of buoy 50. The tanker may be arranged for unloading hydrocarbons to a pipeline 56 or conduit 56 may be a riser from a subsea well for transferring hydrocarbons to a storage vessel. Floating hoses 60 run from swivel 54 to the side of the vessel 100 to storage holds in the vessel. A portion of the loading hoses 60 form a "U"-shape 62, as they enter the vessel 100. For the arrangement of FIG. 3, it is preferred to tether the oil/water detector buoy 30 at the "U"-shape 62 of floating hoses 60. This arrangement advantageously places the buoy 30 in the path of any oil leaking from loading hoses 70, swivel 54 or floating hoses 60. A control module 36' and antenna 38' on vessel 100 provide communication between oil/water buoy 30 and vessel 100 via antennas 32 and 38'. Alternatively, oil/water detector buoy 30 may be tethered from the side of the vessel 100 as a rail tethered buoy 30', where the tether is connected on the down current end (that is stem end) of the vessel as compared to the position where the floating hoses 60 enter the vessel.

Figure 4:
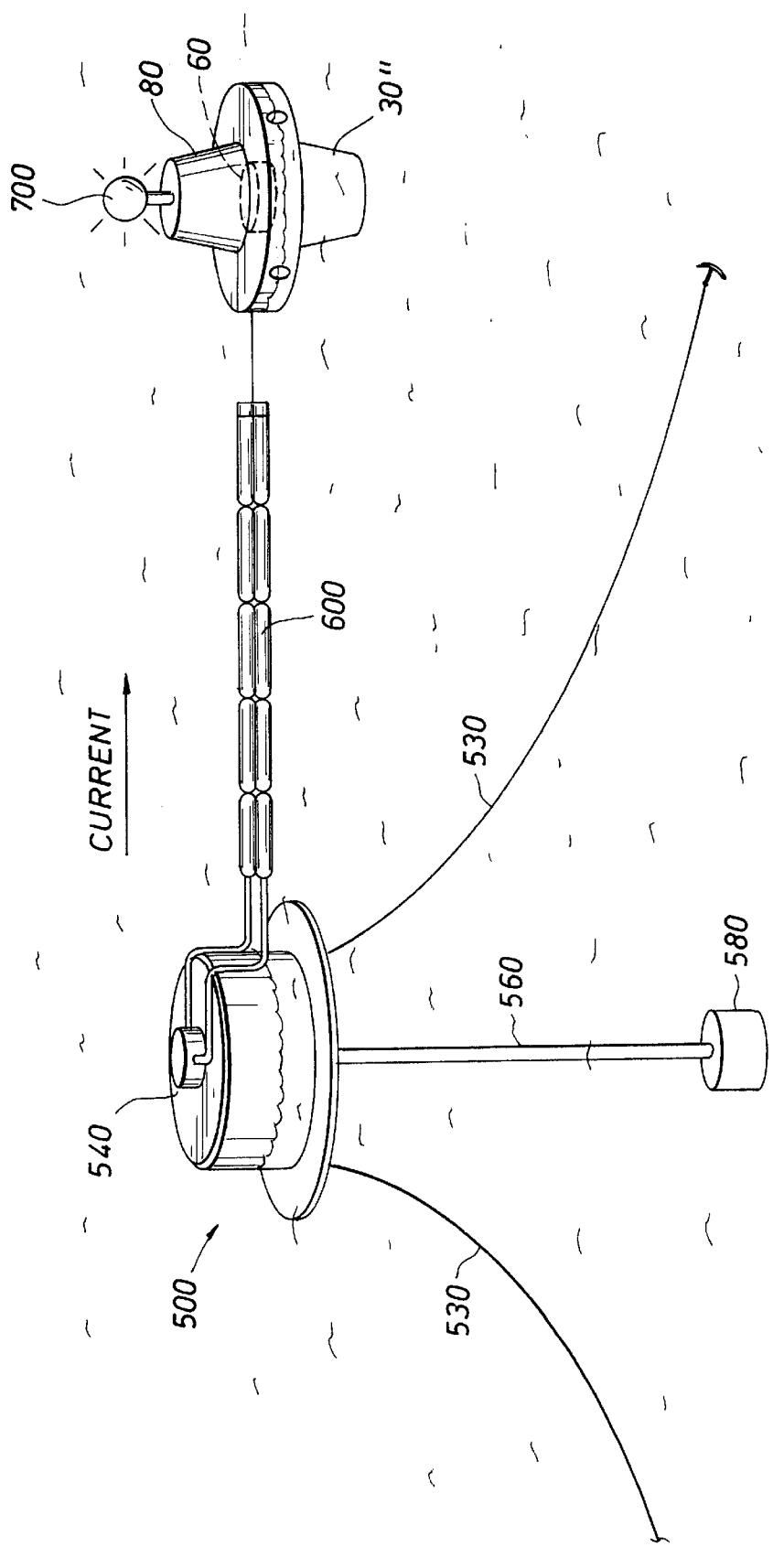
FIG. 4 is an illustration of the invention where the oil/water detection buoy is tethered to the end of floating hoses of a CALM buoy and further illustrating an alternative beacon on the buoy.

The oil/water detector buoy 30 may be used at other locations and in alternative arrangements. For example, the detector buoy may detect oil from an oil source down current from a spread moored vessel, a marine loading arm terminal, a pier or jetty, or an offshore floating or fixed structure for a hydrocarbon well. FIG. 4 illustrates one example of such alternative arrangements. A CALM buoy 500 is anchored to the sea floor by anchor legs 530. A riser 560 extends from a subsea well 580 to a swivel 540 of the buoy 500. A loading hose 600 floats on the sea surface down current, until it is needed for coupling with a storage vessel. While in the condition of FIG. 4, an oil/water sensor buoy 30" is tethered to the end of loading hose 600 which places it in the path of any oil leaking from the swivel 540 or the hose 600. Alternative to the electromagnetic antenna of the buoy 30 in FIG. 2, other signal producing devices can be connected to the sensor 60 and electronics module 80 of the buoy 30". For example, a strobe light 700 may be provided, or a horn could be provided, to alert personnel from passing ships or planes or the like that oil is leaking from the buoy 500, swivel 540 or hose 600.

While preferred embodiments of the present invention have been illustrated and/or described in some detail, modifications and adaptions of the preferred embodiments will occur to those skilled in the art. Such modifications and adaptations are within the spirit and scope of the present invention.

What is claimed is:

1. A system for detecting sea surface oil sheens from a leaking oil source comprising;
    a buoyant body arranged and designed to be self-righting in heavy seas including,
    a submerged section including ballasting material,
    a buoyant section coupled to said submerged section, said buoyant section being partially submerged and partially extending above the sea surface,
    said buoyant section including an oil/water sensor arranged to contact with the sea surface and which produces an oil/water signal representative of the presence of oil floating on said sea surface,
    an electronics module and a sending antenna carried by said buoyant section, with said electronics module being in communication with said oil/water sensor and responsive to said oil/water signal to produce an electromagnetic signal on said sending antenna,
    a receiving antenna coupled to a receiving electronics module placed at a remote body for receiving said electromagnetic signal and for producing a signal at said remote body indicative of oil on said sea surface at said buoyant body,
    a coupling between said remote body and said buoyant body, whereby said buoyant body and said oil/water sensor of said buoyant body floats down-current in the path of said leaking oil source, and wherein
        said receiving antenna and said receiving electronics module are disposed on a vessel which is tethered to a mooring buoy,
        said mooring buoy being anchored to a seabed and being coupled to a hydrocarbon conduit via a fluid swivel, said mooring buoy having a floating loading hose arranged and designed to transfer hydrocarbons between said fluid swivel and said vessel, with a portion of said floating loading hose forming a "U" shape at an entrance point of the vessel, and said buoyant body being tethered at the "U" portion of said floating loading hose whereby said oil/water sensor of said buoyant body is placed down current of said "U" shape said floating loading hose.

2. The system of claim 1 wherein, said electronics module is battery powered by means of one or more batteries disposed on said buoyant body.

3. The system of claim 2 wherein, one or more batteries are disposed in said submerged section of said buoyant body and provide at least partial ballasting material for said body.

4. The system of claim 1 wherein, said buoyant section has a channel at sea surface level when said buoyant body is in the sea, where sea surface water is in said channel.

5. The system of claim 1 wherein, said remote body is a FPSO and said coupling is a tether between said buoyant body and a stem position of said FPSO.

6. A system for detecting sea surface oil sheens comprising;

a buoyant buoy arranged and designed to be self-righting in heavy seas and having an oil/water sensor which produces an oil/water signal representative of the presence of oil floating on said sea surface and having an electronics module and a beacon coupled to said oil/water sensor which generates a signal on said beacon which corresponds to said oil/water signal, a receiving antenna coupled to a receiving electronics module placed on a vessel which is coupled to a mooring buoy, said mooring buoy being anchored to a seabed and being coupled to a hydrocarbon conduit via a fluid swivel, said mooring buoy having a floating loading hose arranged and designed to transfer hydrocarbons between said fluid swivel and said vessel, with a portion of said floating loading hose forming a "U" shape at an entrance point of the vessel, said buoyant body being tethered to float down-current of said "U" shape of said floating hose, whereby said receiving antenna with said receiving electronics module on said vessel in response to said signal on said beacon produces a signal representative of oil on said sea surface at said buoyant body.

7. The system of claim 6 wherein, said buoyant body is tethered at the "U" portion of said floating loading hose.

8. The system of claim 6 wherein, said buoyant body is tethered at the side of said vessel and arranged to float down current of said "U" shape of said floating loading hose.

9. A system for detecting oil sheens on a sea surface comprising, a buoyant body arranged and designed to be self-righting in heavy seas and having an oil/water sensor which produces an oil/water signal representative of the presence of oil floating on said sea surface and having an electronics module and a beacon coupled to said oil/water sensor which generates a signal on said beacon which corresponds to said oil/water signal, said mooring buoy being anchored to a seabed and being coupled to a hydrocarbon conduit via a fluid swivel, said mooring buoy having a floating loading hose which is arranged and designed to transfer hydrocarbons between said fluid swivel and said vessel, said floating loading hose floating down current from said mooring buoy, said buoyant body being coupled to said floating loading hose for generating a beacon signal when an oil sheen on said sea surface is detected.

10. The system of claim 9 wherein, said beacon signal is a light signal.

11. The system of claim 9 wherein, said beacon signal is an audio signal.

12. The system of claim 9 wherein, said beacon signal is an electromagnetic signal.

13. A system for detecting sea surface oil sheens from a leaking oil source comprising;

a buoyant body arranged and designed to be self-righting in heavy seas including, a submerged section including ballasting material, a buoyant section coupled to said submerged section, said buoyant section being partially submerged and partially extending above the sea surface, said buoyant section including an oil/water sensor arranged to contact with the sea surface and which produces an oil/water signal representative of the presence of oil floating on said sea surface, an electronics module and a sending antenna carried by said buoyant section, with said electronics module being in communication with said oil/water sensor and responsive to said oil/water signal to produce an electromagnetic signal on said sending antenna, a receiving antenna coupled to a receiving electronics module placed at a remote body for receiving said electromagnetic signal and for producing a signal at said remote body indicative of oil on said sea surface at said buoyant body, a coupling between said remote body and said buoyant body, whereby said buoyant body and said oil/water sensor of said buoyant body floats down-current in the path of said leaking oil source, wherein said receiving antenna and said receiving electronics module are disposed on a vessel which is tethered to a mooring buoy, said mooring buoy being anchored to a seabed and being coupled to a hydrocarbon conduit via a fluid swivel, said mooring buoy having a floating loading hose arranged and designed to transfer hydrocarbons between said fluid swivel and said vessel, with a portion of said floating loading hose forming a "U" shape at an entrance point of the vessel, said buoyant body being tethered to the side of said vessel and arranged to float down current of said "U" shape of said floating loading hose.

* * * * *